(12) United States Patent
Yamane et al.

(10) Patent No.: US 10,035,812 B2
(45) Date of Patent: Jul. 31, 2018

(54) PERFLUOROPOLYETHER-MODIFIED POLYSILAZANE, MAKING METHOD, SURFACE TREATING AGENT, AND TREATED ARTICLE

(71) Applicant: Shin-Etsu Chemical Co., Ltd., Tokyo (JP)

(72) Inventors: Yuji Yamane, Annaka (JP); Noriyuki Koike, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 56 days.

(21) Appl. No.: 14/062,220

(22) Filed: Oct. 24, 2013

(65) Prior Publication Data

US 2014/0147680 A1 May 29, 2014

(30) Foreign Application Priority Data

Nov. 26, 2012 (JP) ................. 2012-257650

(51) Int. Cl.
*C07F 7/10* (2006.01)
*C07F 7/18* (2006.01)

(52) U.S. Cl.
CPC .............. *C07F 7/10* (2013.01); *C07F 7/1836* (2013.01)

(58) Field of Classification Search
CPC .......... C07F 7/10; C07F 7/1836; C12N 15/85; C12N 15/86; C12N 2710/10041
See application file for complete search history.

(56) References Cited

U.S. PATENT DOCUMENTS

2010/0015453 A1*  1/2010  Yamaguchi ........ C08G 65/3255
                                                428/428
2010/0324250 A1*  12/2010 Yamaguchi ............ C08G 77/46
                                                528/25

FOREIGN PATENT DOCUMENTS

JP        2010-43251 A       2/2010

* cited by examiner

*Primary Examiner* — Michael B Nelson
(74) *Attorney, Agent, or Firm* — Birch, Stewart, Kolasch & Birch, LLP

(57) ABSTRACT

A perfluoropolyether-modified polysilazane of silazane units of formula (1), where Q is a divalent organic group, p and q are an integer of at least 1, r and s are an integer of at least 0, and x is an integer of 1 to 3. A surface treating agent comprising the polysilazane is improved in water/oil repellency, surface slip and smear wipe-off.

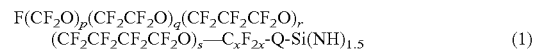

(1)

7 Claims, No Drawings

PERFLUOROPOLYETHER-MODIFIED POLYSILAZANE, MAKING METHOD, SURFACE TREATING AGENT, AND TREATED ARTICLE

CROSS-REFERENCE TO RELATED APPLICATION

This non-provisional application claims priority under 35 U.S.C. § 119(a) on Patent Application No. 2012-257650 filed in Japan on Nov. 26, 2012, the entire contents of which are hereby incorporated by reference.

TECHNICAL FIELD

This invention relates to a novel perfluoropolyether-modified polysilazane, a method for preparing the same, a surface treating agent comprising the same, and an article treated with the agent.

BACKGROUND ART

Polysilazanes are Si—N—Si linkage-bearing compounds having very high reactivity. By virtue of their reactivity, they are often used as surface treating agents. Owing to high reactivity, they are difficult to handle and tend to gel or build up their molecular weight during synthesis.

Perfluoropolyether-modified polysilazanes are generally produced by converting a perfluoropolyether having functionality at one end into silazane. This is because gelation can often occur during the reaction if a perfluoropolyether having functionality at both ends is used. While perfluoropolyethers having $[(CF_2O)_p(CF_2CF_2O)_q]$ in their backbone structure are believed effective for wiping off smears, only dual end functional perfluoropolyethers are commercially available.

Patent Document 1 discloses perfluoropolyether-modified polysilazanes having the formula (A):

$$F(C_xF_{2x}O)_mC_yF_{2y}\text{-}Q\text{-}Si(NH)_{1.5} \quad (A)$$

wherein Q is a divalent organic group, m is an integer of at least 1, x and y each are an integer of 1 to 3. They exhibit excellent water repellency, oil repellency and alkaline durability. However, those perfluoropolyether-modified polysilazanes used in Examples of Patent Document 1 are still unsatisfactory in surface slip and smear wipe-off.

In the industry, there is a demand for a surface treating agent having better properties including water/oil repellency, surface slip and smear wipe-off.

CITATION LIST

Patent Document 1: JP-A 2010-043251 (US 20100015453)

DISCLOSURE OF INVENTION

An object of the invention is to provide a novel perfluoropolyether-modified polysilazane having high reactivity and useful as a surface treating agent; a method for preparing the modified polysilazane; a surface treating agent comprising the modified polysilazane, having improved properties including water/oil repellency, surface slip and smear wipe-off; and an article treated with the surface treating agent.

The inventors have found that a perfluoropolyether-modified polysilazane consisting of silazane units having the following formula (1) has high reactivity and is useful as a surface treating agent having improved properties including water/oil repellency, surface slip and smear wipe-off.

$$F(CF_2O)_p(CF_2CF_2O)_q(CF_2CF_2CF_2O)_r\text{-} \\ (CF_2CF_2CF_2CF_2O)_s\text{---}C_xF_{2x}\text{-}Q\text{-}Si(NH)_{1.5} \quad (1)$$

Herein Q is a divalent organic group, p and q each are an integer of 1 or greater, r and s each are an integer of 0 or greater, respective recurring units may be randomly bonded, and x is an integer of 1 to 3.

The perfluoropolyether-modified polysilazane can be prepared by starting with a perfluoropolyether compound having carboxyl at both ends. This perfluoropolyether compound is fluorinated partially (at one end), thereby obtaining a mixture of mono-terminated polymer and nonfunctional polymer. Only the mono-terminated polymer is extracted from the mixture via adsorption treatment. Using this mono-terminated polymer, the inventors have succeeded in synthesizing one end functional perfluoropolyether-modified polysilazane.

Notably, Patent Document 1 discloses silazanes comprising branched recurring units represented by the formula:

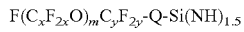
$$\begin{array}{c} \text{---CF---CF}_2\text{O---} \\ | \\ \text{CF}_3 \end{array}$$

and their effects, but not perfluoropolyether-modified silazanes having $[(CF_2O)_p(CF_2CF_2O)_q]$ in their backbone structure. In the silazanes of the invention, $CF_2O$ units and $CF_2CF_2O$ units are essential, all $CF_2CF_2O$, $CF_2CF_2CF_2O$ and $CF_2CF_2CF_2CF_2O$ units are straight, and neither branched perfluoroether units nor branched perfluoropolyether units are contained.

Accordingly, in one aspect, the invention provides a perfluoropolyether-modified polysilazane consisting of silazane units having the formula (1):

$$F(CF_2O)_p(CF_2CF_2O)_q(CF_2CF_2CF_2O)_r\text{-} \\ (CF_2CF_2CF_2CF_2O)_s\text{---}C_xF_{2x}\text{-}Q\text{-}Si(NH)_{1.5} \quad (1)$$

wherein Q is a divalent organic group, p and q each are an integer of at least 1, r and s each are an integer of at least 0, respective recurring units may be randomly bonded, and x is an integer of 1 to 3.

In formula (1), the perfluoropolyether moiety of the formula:

$$F(CF_2O)_p(CF_2CF_2O)_q(CF_2CF_2CF_2O)_r\text{-} \\ (CF_2CF_2CF_2CF_2O)_s\text{---}$$

is preferably represented by the formula:

$$F(CF_2O)_p(CF_2CF_2O)_q\text{---}$$

wherein p and q are as defined above, and respective recurring units may be randomly bonded.

In formula (1), Q is preferably a divalent hydrocarbon group of 2 to 12 carbon atoms which may be separated by one or more structures selected from the class consisting of an amide bond, ether bond, ester bond and diorganosilylene group.

In another aspect, the invention provides a method for preparing the perfluoropolyether-modified polysilazane, comprising the steps of (1) partially fluorinating a perfluoropolyether compound having carboxyl groups at both ends, (2) modifying the carboxyl group at one end and silylating into a reactive silyl group, and (3) converting the reactive silyl group to a silazane.

In a third aspect, the invention provides a surface treating agent comprising the perfluoropolyether-modified polysilazane defined above.

In a fourth aspect, the invention provides a cured film comprising the perfluoropolyether-modified polysilazane defined above.

In a fifth aspect, the invention provides an article comprising a substrate having a surface and a cured film of the perfluoropolyether-modified polysilazane on the substrate surface. The substrate is typically a touch panel, anti-reflective coating, display cover glass, tempered glass, transportation vehicle glass, hardcoat film, display cover film, quartz, optical member, sanitary member, glass tableware, or building member.

Advantageous Effects of Invention

The surface treating agent comprising a perfluoropolyether-modified silazane according to the invention is improved in surface slip and smear wipe-off over the prior art silazane-based water/oil repellent treating agents. The reaction rate is higher than the prior art hydrolyzable water/oil repellent treating agents.

DESCRIPTION OF PREFERRED EMBODIMENTS

Polysilazane

The perfluoropolyether-modified polysilazane of the invention consists of units having the formula (1).

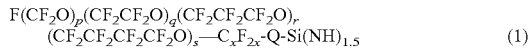  (1)

Herein Q is a divalent organic group, p and q each are an integer of at least 1, r and s each are an integer of at least 0, respective recurring units may be randomly bonded, and x is an integer of 1 to 3.

In formula (1), Q stands for a divalent organic group, preferably a divalent hydrocarbon group of 2 to 12 carbon atoms which may be separated by one or more structures selected from among an amide bond, ether bond, ester bond and diorganosilylene group. Illustrative examples include alkylene groups of 2 to 12 carbon atoms, preferably 2 to 4 carbon atoms such as —CH$_2$CH$_2$— and —CH$_2$CH$_2$CH$_2$—; oxyalkylene groups of 2 to 12 carbon atoms, preferably 2 to 4 carbon atoms such as —CH$_2$OCH$_2$CH$_2$CH$_2$—; ester groups of the formula: —COOR'— (wherein R' is C$_1$-C$_{11}$, preferably C$_1$-C$_3$ alkyl) such as —CO$_2$—(CH$_2$)$_3$—; amide groups of the formula: —CONR— wherein R is hydrogen or C$_1$-C$_5$, preferably C$_1$-C$_3$ lower alkyl such as methyl, ethyl or propyl; diorganosilylene groups of the formula: —SiR"$_2$— wherein R" is C$_1$-C$_6$, preferably C$_1$-C$_3$ alkyl; and a combination comprising one or more of the foregoing.

The subscript p is an integer of at least 1, preferably 1 to 80, and more preferably 3 to 30; q is an integer of at least 1, preferably 1 to 80, and more preferably 3 to 30; r is an integer of at least 0, preferably 0 to 20, and more preferably 0 to 5; s is an integer of at least 0, preferably 0 to 20, and more preferably 0 to 5; respective recurring units may be randomly bonded; and x is an integer of 1 to 3, especially equal to 1.

Preferred are polysilazanes in which the perfluoropolyether moiety of the formula:

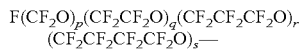

is represented by the following formula:

wherein p and q are as defined above, and respective recurring units may be randomly bonded.

Illustrative examples of the unit having formula (1) are shown below. Herein, Ph stands for phenyl and respective recurring units may be randomly bonded.

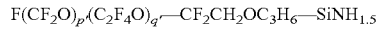

(p'=3, q'=3)

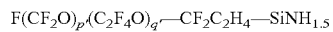

(p'=3, q'=3)

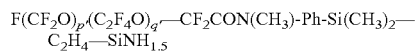

(p'=3, q'=3)

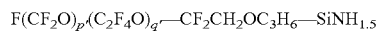

(p'=9, q'=8)

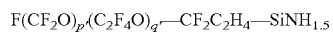

(p'=9, q'=8)

(p'=9, q'=8)

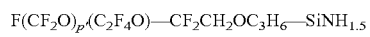

(p'=5, q'=12)

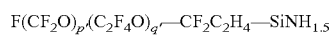

(p'=5, q'=12)

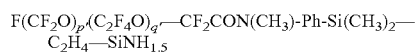

(p'=5, q'=12)

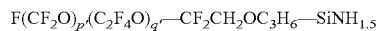

(p'=13, q'=12)

(p'=13, q'=12)

(p'=13, q'=12)

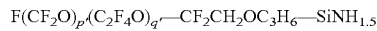

(p'=15, q'=19)

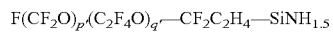

(p'=15, q'=19)

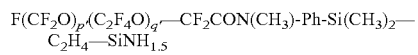

(p'=15, q'=19)

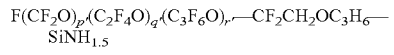

(p'=12, q'=11, r'=1)

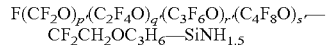

(p'=12, q'=11, r'=1, s'=1)

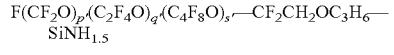

(p'=12, q'=11, s'=1)

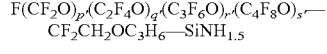

(p'=10, q'=8, r'=5, s'=4)

Notably, the molecular structure of the perfluoropolyether-modified polysilazane is not limited to the above-exemplified structures.

Preparation Method

The perfluoropolyether-modified polysilazane may be prepared, for example, by a method comprising the steps of:

(1) partially fluorinating a perfluoropolyether compound having carboxyl groups at both ends, (2) modifying the carboxyl group at one end and silylating into a reactive silyl group, and (3) converting the reactive silyl group to a silazane.

The step (1) is to partially fluorinate a perfluoropolyether compound capped with carboxyl at both ends. Examples of the perfluoropolyether compound capped with carboxyl at both ends are shown below wherein respective recurring units may be randomly bonded.

HOOC—$CF_2O$—$(CF_2O)_{p'}$-$C_2F_4O)_{q'}$—$CF_2COOH$ (p'=3, q'=3)

HOOC—$CF_2O$—$(CF_2O)_{p'-1}(C_2F_4O)_{q'}$—$CF_2COOH$ (p'=9, q'=8)

HOOC—$CF_2O$—$(CF_2O)_{p'-1}(C_2F_4O)_{q'}$—$CF_2COOH$ (p'=5, q'=12)

HOOC—$CF_2O$—$(CF_2O)_{p'-1}(C_2F_4O)_{q'}$—$CF_2COOH$ (p'=13, q'=12)

HOOC—$CF_2O$—$(CF_2O)_{p'-1}(C_2F_4O)_{q'}$—$CF_2COOH$ (p'=15, q'=19)

HOOC—$CF_2O$—$(CF_2O)_{p'-1}(C_2F_4O)_{q'}(C_3F_6O)_{r'}$—$CF_2COOH$ (p'=12, q'=11, r'=1)

HOOC—$CF_2O$—$(CF_2O)C_{p'-1}(C_2F_4O)_{q'}(C_3F_6O)_{r'}(C_4F_8O)_{s'}$—$CF_2COOH$ (p'=12, (q'=11, r'=1, s'=1)

HOOC—$CF_2O$—$(CF_2O)_{p'-1}(C_2F_4O)_{q'}(C_2F_8O)_{s'}$—$CF_2COOH$ (p'=12, q'=11, s'=1)

HOOC—$CF_2O$—$(CF_2O)_{p'-1}(C_2F_4O)_{q'}(C_3F_6O)_{r'}(C_4F_8O)_{s'}$—$CF_2COOH$ (p'=10, q'=8, r'=5, s'=4)

The step of partially fluorinating a perfluoropolyether compound capped with carboxyl at both ends may be carried out by feeding fluorine gas to effect fluorinating reaction. In this reaction, the amount of fluorine gas fed may be adjusted to control a degree of fluorination for thereby achieving an appropriate degree of incorporation of terminal —$CF_3$ groups. The degree of incorporation of terminal —$CF_3$ groups is preferably at least 50 mol %, more preferably at least 60 mol %, even more preferably at least 7.0 mol %, and most preferably 70 to 80 mol %, based on the entire COOH groups. As long as the degree of incorporation is at least 50 mol %, the reaction product is a mixture of a perfluoropolyether compound having carboxyl at one end and a perfluoropolyether compound free of terminal carboxyl groups (i.e., nonfunctional polymer).

The mixture may be separated by adsorption treatment, fractionation or molecular distillation. For example, adsorption treatment may be carried out using an acid adsorbent such as anion-exchange resin. First a dispersion of an anion-exchange resin in a fluorinated solvent is combined with the mixture, whereby a polymer having carboxyl at one end is adsorbed to the anion-exchange resin. By this step, the nonfunctional polymer may be removed. Thereafter, the anion-exchange resin is washed with a fluorinated solvent and strong acid. During the washing step, the strong acid is adsorbed to the anion-exchange resin whereas the polymer having carboxyl at one end is eluted in the fluorinated solvent. Since the polymer having carboxyl at one end is eluted in this step, a mixture containing the polymer capped with carboxyl at one end in a high concentration is obtainable.

In the case of fractionation or molecular distillation, since a compound having less functional groups at molecular ends evaporates under milder conditions, the nonfunctional polymer is first separated, and the polymer capped with carboxyl at one end is then separated. Then a mixture containing the polymer capped with carboxyl at one end in a high concentration is obtainable. Suitable molecular distillation stills used in molecular distillation include a pot molecular distillation still, falling-film molecular distillation still, centrifugal molecular distillation still, and experimental centrifugal molecular distillation still. Although treating conditions may be selected as appropriate, a pressure of $10^{-5}$ Pa to $10^{-1}$ Pa and a temperature of 100 to 400° C. are preferred. It is acceptable to combine adsorption treatment with molecular distillation. A mixing ratio of the polymer capped with carboxyl at one end and the nonfunctional polymer may be determined from a molar ratio of —$CF_3$ groups to —$CF_2COOH$ groups as measured by $^{19}F$-NMR.

In step (2), the terminal carboxyl group on the partially fluorinated perfluoropolyether compound resulting from step (1) is modified. For example, the terminal carboxyl group on the compound is first converted to a hydroxyl group, whereupon a linking group in the form of a divalent $C_2$-$C_{12}$ hydrocarbon group, which may be separated by at least one structure selected from among an amide bond, ether bond, ester bond and diorganosilylene group, and a terminal aliphatic unsaturated group may be introduced. Exemplary aliphatic unsaturated groups include $C_2$-$C_{12}$ alkenyl groups such as vinyl, allyl, and propenyl. Exemplary compounds capable of introducing such a group include allyl halides such as allyl bromide.

The introduction step may accord with any well-known methods. For example, a fluorooxyalkylene-bearing polymer containing an ether bond-containing linking group: —$CH_2OCH_2CH_2$— as the linking group in the form of a divalent hydrocarbon group may be prepared by first subjecting the mixture of a polymer capped with carboxyl at one end to reduction with a metal hydride or catalytic hydrogenation with a noble metal catalyst, for thereby obtaining a mixture of a polymer capped with hydroxyl at one end. Next, an aliphatic unsaturated group is introduced into the hydroxyl-capped polymer at the one end. The introduction of an aliphatic unsaturated group into the hydroxyl group may be carried out using any well-known methods. For example, the polymer capped with hydroxyl at one end is reacted with an allyl halide (e.g., allyl bromide) in the presence of tetrabutylammonium hydrogensulfate, whereupon sodium hydroxide is added dropwise to the reaction mixture to make it alkaline, for thereby introducing the aliphatic unsaturated group (e.g., allyl) at the end.

Next, the aliphatic unsaturated group is converted to a reactive silyl group. A chlorosilane is reacted with the aliphatic unsaturated group by the well-known method, for thereby introducing a silyl group at the end.

In the final step (3), the silyl group on the polymer capped with silyl at one end is converted into a silazane form, yielding the desired compound. Conversion to silazane form may be achieved by the well-known method of blowing ammonia gas.

Surface Treating Agent

A third embodiment of the invention is a surface treating agent comprising the perfluoropolyether-modified polysilazane defined above as an active ingredient. It is acceptable to use a partial hydrolytic condensate of the perfluoropolyether-modified polysilazane.

The surface treating agent may be diluted with a solvent. Suitable solvents include fluorine-modified aromatic hydrocarbon solvents such as m-xylene hexafluoride and benzotrifluoride; fluorine-modified ether solvents such as methyl perfluorobutyl ether, ethyl perfluorobutyl ether and perfluoro(2-butyltetrahydrofuran); and fluorine-modified alkylamine solvents such as perfluorotributylamine and perfluorotripentylamine. Inter alia, m-xylene hexafluoride and ethyl perfluorobutyl ether are preferred for solubility and wettability. These solvents may be used alone or in admixture of two or more. A solvent capable of uniformly dissolving the ingredient is preferred.

The amount of the solvent used is not particularly limited. An optimum concentration varies with a particular surface treating method. Preferably the solvent is used in such amounts that the concentration of solids (i.e., perfluoropolyether-modified polysilazane) may be 0.001 to 10% by weight, more preferably 0.01 to 5% by weight of the (diluted) surface treating agent.

Cured Film

A substrate or support is surface treated with the surface treating agent by any well-known methods. The surface treating agent is applied to the substrate or support surface by brush coating, dipping, spray coating, evaporation or the like. The resulting coating cures at normal temperature to form a cured film on the substrate or support surface. The cured film is tenaciously bonded to the substrate or support surface probably because silazane bonds are hydrolyzed to create silanol groups which are active enough to enhance bond strength.

Although the coating as applied to the substrate or support cures at normal temperature as mentioned above, the cure step may be accelerated by heating the coating such as by hot air blowing or IR irradiation.

In this regard, a silanol condensation catalyst may be added to the surface treating agent prior to application. Suitable condensation catalysts include organotin compounds such as dibutyltin dimethoxide and dibutyltin dilaurate; organotitanium compounds such as tetra-n-butyl titanate; organic acids such as acetic acid and methanesulfonic acid; and mineral acids such as hydrochloric acid and sulfuric acid. The cure step is further accelerated particularly when acetic acid, tetra-n-butyl titanate or dibutyltin dilaurate is previously added to the treating agent. The amount of the condensation catalyst added may be a catalytic amount, preferably 0.001 to 5 parts by weight, more preferably 0.01 to 1 part by weight per 100 parts by weight of the perfluoropolyether-modified polysilazane.

Also, when an acrylic or methacryloxy group has been introduced into the organic group bonded to the silazane unit, the crosslinking density may be further increased by irradiation of UV or EB following normal temperature cure.

The substrate which is treated with the surface treating agent is not particularly limited. Substrates of various materials including paper, fabric, metals and metal oxides, glass, plastics, porcelain, and ceramics may be used. Exemplary substrates include paper, fabric, metals, glass, plastics, ceramics, etc. when the surface treating agent is a water/oil repellent agent; pressure-sensitive adhesive tape, resin-molding molds, rolls, etc. when the surface treating agent is a parting agent; and paper, fabric, metals, glass, plastics, ceramics, etc. when the surface treating agent is an antifouling agent.

Besides, the surface treating agent is also effective for modifying the flow and dispersion of paint additives, resin modifiers, and inorganic fillers, and for improving the lubricity of tape and film.

When the cured film is formed on the surface of a substrate or article, the film thickness may be selected as appropriate depending on the type of substrate.

Article

The surface treating agent may be used for the surface treatment of various articles. A fourth embodiment of the invention is an article comprising a substrate (i.e., article-constituting substrate) and a cured film of the perfluoropolyether-modified polysilazane formed on the substrate surface.

Specifically, a cured film may be formed on the surface of any of the following articles for the purpose inherent to a particular article. The cured film is useful as, for example, fingerprint resistant coating on touch panels (in smart phones, tablet PCs, smart TVs, portable media players, and advertising displays), antireflective coating on touch panel surface, tempered glass, hard coat film and resin substrates; fingerprint resistant, water/oil repellent coating on glazing in transporting vehicles such as automobiles, aircraft, and trains, paint coatings, and interiors; antifouling, light peel coating on optical members of quartz or the like; water repellent or antifouling coating on sanitary articles such as bathtubs and basins; antifouling coating on industrial glass and glass tableware; water repellent, antifouling coating on exterior building members such as wall members; grease-proof coating on interior building members such as kitchen items; antifouling coating on glass (e.g., window glass, headlamp cover) in transporting vehicles such as automobiles, aircraft, and trains; water/oil repellent, weather resistant, antifouling and antisticking coating in telephone booths; and water/oil repellent, fingerprint resistant coating on fine arts or the like. Among these, the surface treating agent finds best use on touch panels, antireflective coating, display cover glass, tempered glass, transportation vehicle glass, hardcoat film, display cover film, quartz, optical members, sanitary items, glass tableware and building members.

EXAMPLE

Examples and Comparative Examples are given below by way of illustration and not by way of limitation.

In Examples, a mixture consisting of 45 mol % of a compound having formula (1a) and 55 mol % of a compound having formula (1b) was used. This mixture was prepared by partially fluorinating a perfluorooxy compound having carboxyl at both ends, using fluorine gas. As fluorination proceeded on the perfluorooxy compound having carboxyl at both ends, one or two end groups were converted to fluorine groups. The contents of respective polymers were determined by separating the carboxyl-containing polymer via adsorption to an acid adsorbent, followed by $^{19}$F-NMR analysis.

$F(CF_2O)_{p'}(C_2F_4O)_{q'}$—$CF_2COOH$      (1a)

$F(CF_2O)_{p'}(C_2F_4O)_{q'}$—$CF_3$      (1b)

(q'/p'=0.9, p'+q'≈17)

Example 1

(i) In a reactor, 400 g of the mixture of 45 mol % of compound (1a) and 55 mol % of compound (1b) was dissolved in 4.0 kg of a fluorinated solvent PF5060 (3M). Then 3.2 kg of an anion-exchange resin B20-HG (Organo Corp.) was added to the solution, which was stirred for 3 hours at 20° C., allowing compound (1a) to be adsorbed to the anion-exchange resin. The anion-exchange resin was then washed with fluorinated solvent PF5060, and mixed with 6 kg of PF5060. An appropriate amount of hydrochloric acid was added to the mixture, which was stirred for 3 hours at 20° C. At the end of stirring, the mixture was allowed to stand for 30 minutes, whereupon it separated into two layers, a lower layer of fluorinated solvent and an upper layer of a mixture of hydrochloric acid and the resin. The fluorinated solvent layer was taken out, from which PF5060 was distilled off, leaving 130 g of a product. On $^{19}$F-NMR analysis, the product was a mixture of 95 mol % of compound (1a) and 5 mol % of compound (1b).

(ii) The mixture resulting from (i), 50 g, was dissolved in a solvent mixture of 100 g of m-xylene hexafluoride and 20 g of tetrahydrofuran. To the solution, 100 g of a 40 wt % toluene solution of bis(2-methoxyethoxy)aluminum sodium hydride was added dropwise. This was followed by stirring for 3 hours at room temperature, addition of an appropriate amount of hydrochloric acid, thorough stirring, and water washing. The lower layer was taken out, from which the solvent was distilled off, leaving 45 g of a liquid product. On $^{19}$F-NMR and $^{1}$H-NMR analyses, the product was a mixture of 95 mol % of compound (2a) and 5 mol % of compound (2b), shown below.

$$F(CF_2O)_{p'}(C_2F_4O)_{q'}\text{---}CF_2CH_2OH \quad (2a)$$

$$F(CF_2O)_{p'}(C_2F_4O)_{q'}\text{---}CF_3 \quad (2b)$$

(q'/p'=0.9, p'+q'≈17)

(iii) A reactor was charged with 40 g of the mixture resulting from (ii), 15 g of allyl bromide, and 0.5 g of tetrabutylammonium hydrogensulfate, which were stirred for 3 hours at 50° C. Then 10.5 g of a 30% sodium hydroxide aqueous solution was added dropwise to the mixture, which was matured for 12 hours at 55° C. Solvent PF5060 and an appropriate amount of hydrochloric acid were added to the mixture, which was stirred and thoroughly washed with water. The lower layer was taken out, from which the solvent was distilled off, leaving 35 g of a liquid product. On $^{19}$F-NMR and $^{1}$H-NMR analyses, the product was a mixture of 95 mol % of compound (3a) and 5 mol % of compound (3b), shown below.

$$F(CF_2O)_{p'}(C_2F_4O)_{q'}\text{---}CF_2CH_2OCH_2CH\!\!=\!\!CH_2 \quad (3a)$$

$$F(CF_2O)_{p'}(C_2F_4O)_{q'}\text{---}CF_3 \quad (3b)$$

(q'/p'=0.9, p'+q∝≈17)

(iv) A reactor was charged with 35 g of the mixture resulting from (iii), 4 g of trichlorosilane, and 0.1 g of a toluene solution of chloroplatinic acid/vinylsiloxane complex (containing $2.5\times10^{-8}$ mol of Pt), which were mixed and matured for 12 hours at 110° C. The unreacted reactants were distilled off in vacuum, leaving 31 g of a liquid silyl product.

(v) In a reactor, 30 g of the silyl product resulting from (iv) was dissolved in 30 g of m-xylene hexafluoride. Dry ammonia gas was blown into the solution. With the supply of ammonia gas, the liquid temperature rose, ammonium chloride formed, and the liquid turned white turbid. Blowing of ammonia gas was continued until the reflux state. With the ammonia gas supply interrupted, stirring was continued for 2 hours under reflux. While nitrogen gas was continuously introduced, the reaction mixture was heated ant stirred for 3 hours for distilling off the excess ammonia gas. Ammonium chloride precipitate was removed by filtration. From the filtrate, m-xylene hexafluoride was distilled off in vacuum, yielding 30 g of a colorless clear liquid. On $^{19}$F-NMR and $^{1}$H-NMR analyses, the liquid was a mixture (designated Composition #1) of 95 mol % of compound (4a) and 5 mol % of compound (4b), shown below.

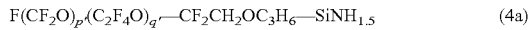

$$F(CF_2O)_{p'}(C_2F_4O)_{q'}\text{---}CF_2CH_2OC_3H_6\text{---}SiNH_{1.5} \quad (4a)$$

$$F(CF_2O)_{p'}(C_2F_4O)_{q'}\text{---}CF_3 \quad (4b)$$

(q'/p'=0.9, p'+q'≈17)

Preparation of Surface Treating Agent and Formation of Cured Film

Composition #1 was dissolved in ethyl perfluorobutyl ether (Novec® 7200 by 3M) in a concentration of 0.1 wt %, yielding a treating bath. A piece (50 mm×100 mm) of chemically strengthened glass (Gorilla® by Corning Inc.) was immersed in the treating bath for 30 seconds, pulled up at a rate of 150 mm/min, and held at room temperature for 1 hour for curing, forming a cured film on the glass.

Comparative Examples 1 to 4

Cured films were formed as in Example 1 except that the following Compounds #1 to #4 were used instead of Composition #1.

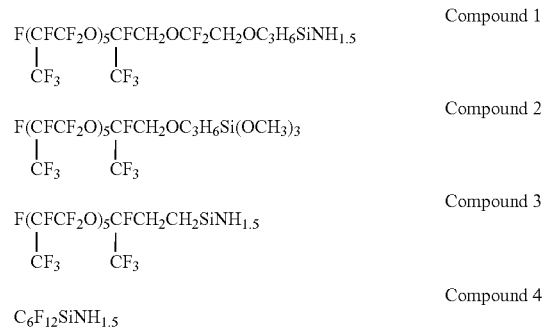

The cured films thus obtained were evaluated by the following tests, with the results shown in Table 1.

Water/Oil Repellent Test

Using a contact angle meter Drop Master (Kyowa Interface Science Co., Ltd.), the cured film on glass was measured for a contact angle with water and a contact angle with oleic acid as an index of water repellency and oil repellency, respectively.

Fingerprint Wipe-Off Test

The cured film on glass was marked with fingerprints and wiped with non-woven fabric Bemcot® (Asahi Chemical Co., Ltd.). A panel of 7 experts rated fingerprint wipe-off according to the following criterion.

A: complete wipe-off within 3 iterations

B: complete wipe-off within 10 iterations

C: no wipe-off

Slip Test

The cured film on glass was rubbed with fabric Bemcot®. A panel of 7 experts rated rubbing feel or slip according to the following criterion.

A: very smooth feel

B: smooth feel

C: rough feel

Abrasion Resistance Test

Using a rubbing tester, the cured film on glass was rubbed under the following conditions before a contact angle with water was measured as above.

Test environment: 25° C., humidity 40%

Rubbing member: The tester had a tip (10 mm×10 mm) in contact with the sample. An 8-ply laminate of Bemcot® was wrapped around the tip and secured thereto with rubber band.

Load: 500 g

Rubbing distance: 40 mm (one way)

Rubbing rate: 1,800 mm/min

Cycle: 5,000 cycles

TABLE 1

| | | Water/oil repellency (contact angle prior to test) | | Tests of surface properties | | Abrasion resistance Water repellency |
|---|---|---|---|---|---|---|
| | Treating agent | Water repellency (°) | Oil repellency (°) | Fingerprint wipe-off Sensory test | Slip Sensory test | after abrasion (°) |
| Example | 1 Composition 1 | 115 | 74 | A | A | 111 |
| Comparative | 1 Compound 1 | 114 | 74 | B | C | 91 |
| Example | 2 Compound 2 | 108 | 68 | C | C | 54 |
| | 3 Compound 3 | 115 | 73 | B | C | 85 |
| | 4 Compound 4 | 111 | 74 | C | C | 83 |

The samples of Comparative Examples were poor in fingerprint wipe-off and slip. Due to poor slip, their resistance to abrasion by fabric was poor as well. Among perfluoropolyethers, those polymers having —(CF$_2$O)$_p$(CF$_2$CF$_2$O)$_q$— structure had excellent slip or smoothness, by virtue of which fingerprint wiping, rubbing feel and abrasion resistance were excellent.

Since the reactive group is silazane, the perfluoropolyether-modified polysilazanes of the invention remain highly reactive with substrates and curable at room temperature without a need for a primer such as SiO$_2$. By virtue of their improved slip over the prior art silazane compounds, fingerprint wipe-off, rubbing feel and abrasion resistance are excellent. Therefore, they are useful as a water/oil repellent layer on optical articles (e.g., touch panel displays and antireflective film), and sanitary articles.

Japanese Patent Application No. 2012-257650 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A perfluoropolyether-modified polysilazane, consisting of silazane units of formula (1'):

F(CF$_2$O)$_p$(CF$_2$CF$_2$O)$_q$—CF$_2$CH$_2$OC$_3$H$_6$—Si(NH)$_{1.5}$ (1')

wherein p and q each are an integer of 3 to 30, p+q is 17 to 34, q/p is 0.9 to 1, and respective recurring units may be randomly bonded.

2. The polysilazane of claim 1, which consists of the following formula:

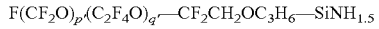

F(CF$_2$O)$_{p'}$(C$_2$F$_4$O)$_{q'}$—CF$_2$CH$_2$OC$_3$H$_6$—SiNH$_{1.5}$ (p'=13, q'=12), wherein respective recurring units may be randomly bonded.

3. A method for preparing the perfluoropolyether-modified polysilazane of claim 1, comprising the steps of:
(1) partially fluorinating a perfluoropolyether compound having carboxyl groups at both ends,
(2) modifying the carboxyl group at one end and silylating into a reactive silyl group, and
(3) converting the reactive silyl group to a silazane.

4. A surface treating agent, comprising the perfluoropolyether-modified polysilazane of claim 1.

5. A cured film, comprising the perfluoropolyether-modified polysilazane of claim 1.

6. An article, comprising a substrate having a surface and the cured film of perfluoropolyether-modified polysilazane of claim 5 on the substrate surface.

7. The article of claim 6, wherein the substrate is a touch panel, anti-reflective coating, display cover glass, tempered glass, transportation vehicle glass, hardcoat film, display cover film, quartz, optical member, sanitary member, glass tableware, or building member.

* * * * *